United States Patent [19]

Spanier et al.

[11] Patent Number: 5,011,679
[45] Date of Patent: Apr. 30, 1991

[54] RAW HIDE HAVING A COATING CONTAINING AN INORGANIC PYROPHOSPHATE

[75] Inventors: Henry C. Spanier, West Milford; Bassey O. Ekpo, Newark, both of N.J.

[73] Assignee: Nabisco Brands, Inc., East Hanover, N.J.

[21] Appl. No.: 358,149

[22] Filed: May 30, 1989

[51] Int. Cl.$^5$ .............................. A61K 7/20
[52] U.S. Cl. .................... 424/57; 428/473; 427/389
[58] Field of Search ............. 424/57; 428/473; 427/389

[56] References Cited

U.S. PATENT DOCUMENTS

| | | | |
|---|---|---|---|
| 2,870,017 | 1/1959 | Barch | 426/563 |
| 2,941,926 | 6/1960 | Salzman et al. | 424/57 |
| 3,112,247 | 11/1963 | Schweizer | 424/52 |
| 3,137,632 | 6/1964 | Schiraldi | 424/49 |
| 3,194,738 | 7/1965 | Harrison et al. | 424/48 |
| 3,375,168 | 3/1968 | Curtin et al. | 424/57 |
| 3,408,918 | 11/1968 | Taly et al. | 426/277 |
| 3,442,604 | 5/1969 | Smith et al. | 424/57 |
| 3,488,419 | 1/1970 | McCune et al. | 424/49 |
| 3,535,420 | 10/1970 | McCune et al. | 424/49 |
| 3,567,459 | 3/1971 | Wruk, III et al. | 99/2 |
| 3,639,569 | 2/1972 | Medcalf, Jr. | 424/48 |
| 3,686,393 | 8/1972 | Woodruff et al. | 424/50 |
| 3,701,830 | 10/1972 | Welwrich et al. | 424/94 |
| 3,871,334 | 3/1975 | Axelrod | 119/29.5 |
| 3,882,257 | 5/1975 | Cagle | 426/274 |
| 3,899,607 | 8/1975 | Miller et al. | 426/285 |
| 3,922,377 | 1/1975 | Whittle | 426/645 |
| 3,927,201 | 12/1975 | Baines et al. | 424/54 |

(List continued on next page.)

FOREIGN PATENT DOCUMENTS

| | | |
|---|---|---|
| 168071 | 12/1953 | Australia . |
| 1233121 | 2/1988 | Canada . |
| 079611 | 5/1983 | European Pat. Off. . |
| 0097476 | 1/1984 | European Pat. Off. . |
| 0236290 | 9/1987 | European Pat. Off. . |
| 0236827 | 9/1987 | European Pat. Off. . |
| 2188548 | 10/1987 | European Pat. Off. . |
| 0249398 | 12/1987 | European Pat. Off. . |
| 0251591 | 1/1988 | European Pat. Off. . |
| 0254452 | 1/1988 | European Pat. Off. . |
| 0288909 | 11/1988 | European Pat. Off. . |
| 0291747 | 11/1988 | European Pat. Off. . |
| 0295116 | 12/1988 | European Pat. Off. . |
| 0297211 | 1/1989 | European Pat. Off. . |
| 0297212 | 1/1989 | European Pat. Off. . |
| 0297213 | 1/1989 | European Pat. Off. . |
| 305283 | 3/1989 | European Pat. Off. . |
| 0309414 | 3/1989 | European Pat. Off. . |
| 0311412 | 4/1989 | European Pat. Off. . |
| 0316079 | 5/1989 | European Pat. Off. . |
| 0319516 | 5/1989 | European Pat. Off. . |
| 330075 | 8/1989 | European Pat. Off. . |
| 2643991 | 3/1978 | Fed. Rep. of Germany . |
| 2749581 | 5/1978 | Fed. Rep. of Germany . |
| 3041237 | 6/1982 | Fed. Rep. of Germany . |
| 3426203 | 7/1984 | Fed. Rep. of Germany . |
| 3417235 | 6/1985 | Fed. Rep. of Germany . |
| 3607480 | 9/1987 | Fed. Rep. of Germany . |
| 8603674 | 7/1986 | PCT Int'l Appl. . |
| 777556 | 6/1957 | United Kingdom . |
| 1122049 | 7/1968 | United Kingdom . |
| 1179343 | 1/1970 | United Kingdom . |
| 1201683 | 8/1970 | United Kingdom . |
| 1386627 | 3/1973 | United Kingdom . |
| 2092000 | 8/1982 | United Kingdom . |
| 2109086 | 6/1983 | United Kingdom . |
| 2180157 | 3/1987 | United Kingdom . |
| 2191500 | 3/1987 | United Kingdom . |
| 2182244 | 5/1987 | United Kingdom . |
| 2194426 | 3/1988 | United Kingdom . |
| 2204487 | 4/1988 | United Kingdom . |
| 2200551 | 8/1988 | United Kingdom . |
| 2201593 | 9/1988 | United Kingdom . |
| 2206027 | 12/1988 | United Kingdom . |

OTHER PUBLICATIONS

Chemical Abstracts 89:74468t (1978).
Chemical Abstracts 83:57001u (1975).
Chemical Abstracts 84:14958q (1976).
Chemical Technology: An Encyclopedic Treatment, Barnes & Nobel Books (1972) (pp. 392–406).
Hides and Skins by Arnold, John R., (pp. 6, 7, 252, 253, 310 and 311).
Footwear and Leather Abstracts, Information Retrieval Ltd., vol. No. 1 (1977) pp. 46, 49 and 61.
North American Packer Hides, Pratt Bros. Co. (1939) (p. 107).
Practical Tanning, Flemming, Louis A. (1910 edn.) (pp. 81 to 83).
The Complete Book of Tanning Skins and Furs, Churchill, James E. (1983 edn.) (pp. 164–168).
Chemical Treatment of Hides and Leather, Partridge, John (1972 edn.) (pp. 2–43).
Practical Leather Technology, Thorstersen, Thomas C. (1985 edn.) (pp. 1 to 41).
Encyclopedia of Chemical Technology, 3rd ed., vol. 14 (1981 edn.) (pp. 200–216).

*Primary Examiner*—Ronald W. Griffin

[57] ABSTRACT

Process for preparing raw hide having a coating containing, at least one inorganic pyrophosphate compound, comprising:
(a) subjecting raw hide to a liquefied coating material containing at least one inorganic pyrophosphate compound, thereby, forming a coating of such liquefied coating material on the raw hide; and
(b) drying the raw hide having a coating containing said at least one inorganic pyrophosphate compound.

The raw hide having a coating containing at least one inorganic pyrophosphate is chewed and/or eaten by dogs, with the result that tartar accumulation on their teeth is reduced or prevented.

5 Claims, No Drawings

U.S. PATENT DOCUMENTS

| | | | |
|---|---|---|---|
| 3,934,002 | 1/1976 | Haefele | 424/54 |
| 3,942,537 | 7/1976 | Evers et al. | 131/278 |
| 3,956,479 | 5/1976 | Bauman | 424/54 |
| 3,957,964 | 5/1976 | Grimm, III | 24/10 |
| 3,959,458 | 5/1976 | Agricola et al. | 424/52 |
| 4,003,971 | 1/1977 | Mannara | 264/9 |
| 4,022,879 | 5/1977 | Dietrich | 424/49 |
| 4,044,158 | 8/1977 | Burkwall, Jr. | 426/271 |
| 4,145,447 | 3/1979 | Fisher et al. | 426/72 |
| 4,153,732 | 8/1979 | Muhler et al. | 426/72 |
| 4,215,149 | 7/1980 | Majlinger | 426/292 |
| 4,244,931 | 1/1981 | Jarvis et al. | 423/266 |
| 4,254,101 | 3/1981 | Demny, Jr. | 424/52 |
| 4,259,358 | 3/1981 | Duthie | 426/46 |
| 4,260,635 | 4/1981 | Fisher | 426/3 |
| 4,314,990 | 2/1982 | Denny, Jr. et al. | 424/52 |
| 4,323,551 | 4/1982 | Farran, Jr. | 424/54 |
| 4,364,925 | 12/1982 | Fisher | 424/50 |
| 4,419,372 | 12/1983 | Greene et al. | 426/805 |
| 4,421,527 | 12/1983 | Wason | 51/308 |
| 4,472,373 | 9/1984 | Ryan | 424/54 |
| 4,513,014 | 4/1985 | Edwards | 426/132 |
| 4,515,770 | 5/1985 | Besic | 424/49 |
| 4,515,772 | 5/1985 | Parran, Jr. et al. | 424/57 |
| 4,532,124 | 7/1985 | Pearce | 424/52 |
| 4,535,725 | 8/1985 | Fisher | 119/29 |
| 4,540,584 | 9/1985 | Someya | 424/156 |
| 4,557,219 | 12/1985 | Edwards | 119/29.5 |
| 4,590,066 | 5/1986 | Parran et al. | 424/52 |
| 4,627,977 | 12/1986 | Gaffar et al. | 424/52 |
| 4,634,448 | 1/1987 | Ajioka et al. | 8/436 |
| 4,674,444 | 6/1987 | Axelrod | 119/29.5 |
| 4,678,662 | 7/1987 | Chan | 424/57 |
| 4,684,518 | 8/1987 | Parran, Jr. et al. | 424/52 |
| 4,702,929 | 10/1987 | Lehn et al. | 426/635 |
| 4,735,808 | 4/1988 | Scaglione et al. | 426/62 |
| 4,771,733 | 9/1988 | Axelrod | 119/29.5 |
| 4,771,773 | 9/1988 | Axelrod | 128/341 |
| 4,795,655 | 1/1989 | Spiel et al. | 426/635 |
| 4,802,444 | 2/1989 | Markham et al. | 119/29 |
| 4,806,340 | 2/1989 | Gaffer et al. | 424/52 |

RAW HIDE HAVING A COATING CONTAINING AN INORGANIC PYROPHOSPHATE

BACKGROUND OF THE ART

1. Field Of The Invention

The invention relates to raw hide strips containing an anti-tartar agent. The invention also relates to a process of preparing such raw hide strips. The invention further relates to a process of preventing tartar on dog's teeth by the dog chewing on such raw hide strips.

2. Background Art

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars. Mature calculus consists of an inorganic portion which is largely calcium phosphate arranged in a hydroxylapatite crystal lattice structure similar to bone, enamel and dentine. An organic portion is also present and consists of desquamated epithelial cells, leukocytes, salivary sediment, food debris and various types of microorganisms. As the mature calculus develops, it becomes visibly white or yellowish in color unless stained or discolored by some extraneous agency. In addition to being unsightly and undesirable from an aesthetic standpoint, the mature calculus deposits are constant sources of irritation of the gingiva and thereby are a contributing factor to gingivitis and other diseases of the supporting structures of the teeth, the irritation decreasing the resistance of tissues to endogeneous and exogenous organisms.

A wide variety of chemical and biological agents have been suggested in the art to retard calculus formation or to remove calculus after it is formed in humans. Mechanical removal of this material is done routinely in humans.

*Chemical Technology: An Encyclopedic Treatment*, Vol. V, Barnes & Noble Books, (1972), pages 392 to 406, is a general disclosure of types of leathers and their uses, and the tanning of leather. Arnold, John R., "Hides And Skins", (1925), pages 6, 7, 252, 253, 310 and 311, is a general disclosure on raw and tanned hides and skins.

Footwear And Leather Abstracts, Information Retrieval Limited, Vol. II, No. 1, (1967), page 61, discloses several methods for the depilation of skins and raw hides and for processing raw hide.

*North American Packer Hides*, Pratt Bros. Co., (1939), page 107, defines rawhide leather as being hides that have been limed, dehaired and stuffed with oil or grease, but otherwise not tanned. Flemming, Louis A., "Practical Tanning", (1910), pages 81 to 83, describes methods of making lace leather.

Churchill, James E., "The Complete Book Of Tanning Skins And Furs", (1983), pages 165, discloses how to make raw hide. Page 166 discloses that rawhide and objects made from rawhide will be eaten by dogs and other animals unless they are treated with mineral oil or another preservative.

Partridge, John, "Chemical Treatment Of Hides And Leather", (1972), pages 2 to 43, deals with the chemical preservation of raw hides and skins and the chemical dehairing of skins and hides. The treatments include: removing hair using a solution of lime containing an inorganic phospho-sulfur compound containing at least one P-S bond; and dehairing using enzymatic action with $K_2HPO_4$ as a pH adjuster.

Thorstensen, Thomas C., "Practical Leather Technology", (1985), pages 1 to 41, deals with the preparation of hides.

Kirk-Othmer, "Encyclopedia Of Chemical Technology", 3rd Ed., Vol. 14, (1981), pages 200 to 216, is a general article on leather. Pages 213, 215 and 216 disclose that polyphosphates are excellent pretannages for vegetable tanning. Optimum molecular weights of the polyphosphates are from 1500 to 2500. Also there is a minimum-effluent vegetable tanning system, known as the Liritan process. The limed and bated hides are treated for 24 hours in a pit with 5 percent of sodium hexametaphosphate (Calgon) solution and sufficient sulfuric acid to achieve a pH of 2.8 at the end of that time. This part of the process has become known as the Calgon pickle. The solution is reused daily, being regenerated with additional Calgon and sulfuric acid, and is discarded only once a year. The treatment presumably prepares the hides for a more rapid vegetable tanning process, and the recommended one with varied concentration of wattle (mimosa) takes 11 days. The tanning liquors are recirculated and reused. Further finishing of leathers that have been prepared by the Liritan process is the same as for those prepared by conventional processes. The Liritan polyphosphate-vegetable combination tannage process, as a non-effluent rapid tannage for sole leather, is used by sole-leather tanneries throughout the world.

U.S. Pat. No. 4,419,372 discloses a simulated raw hide product for dogs. In U.S. Pat. No. 3,408,918, a solution of phosphoric acid is used to neutralize excess calcium in limed hide pieces. U.S. Pat. No. 3,922,377 discloses a heat-processed, dehydrated, bacteriologically-stable pork rind product capable of rapid rehydration. The rehydrated rind is formulated in a pork sausage which includes sodium polyphosphate. German Patent No. 3,426,203 discloses a chewing article for dogs consisting of 92 volume parts of raw skin, 4 volume parts of lime and 4 volume parts of feed salts mixture containing (per 100g) 700 mg of potassium, 1500 mg of carbonate, 1000 mg of calcium, 110 mg of phosphate, 40 mg of iron and 1 mg of iodine. The article is prepared from cow skin by stripping the skin, and subjecting the subcutaneous material to neutralization to pH 6, treating with a solution of iodine-containing feed salt and lime, shaping to form the article and drying.

U.S. Pat. No. 4,145,447 discloses a hard, unit-integral, unitized, self-contained, compact, cgew-resistant nutritionally balanced animal food product having a density of at least about 0.5 oz./in.$^3$, a final water content of at least about 5.5 percent by weight, and a breaking force of at least about 60 psi. The animal food contains, for example, dried meals, dried fish, dried dairy products, fish meal, fish flour, cereals, flours, carbohydrates, dried fruits, etc., with or without food additives or supplements such as vitamins, minerals, medicinals, etc., for example chemicals, enzymes, etc., capable of removing plaque or tartar from the animals's teeth, etc.

U.S. Pat. No. 4,044,158 discloses the use of tetrasodium pyrophosphate as a chelating agent in semi-moist pet foods. The neutral chelating agent is used in a semi-moist pet food having a pH of from 6.3 to 7.2 and which comprises about 5 to about 50 percent by weight meat or meat by-products, about 15 to about 50 percent moisture, and about 1 percent to about 26 percent by weight vegetable protein. The vegetable protein, an amylaceous material, and the chelating agent, it is taught, forms a composition which replaces part of the caseinate binder customarily present in a semi-moist pet food. No mention is made of any antitartar effectiveness of the pet food.

U.S. Pat. No. 4,215,149 discloses a process for maintaining the palatability of a pet food by coating particulates having a moisture content of less than 15 percent with fat and then with a monoalkali metal or monoalkaline earth metal salt of phosphoric acid to make the food more palatable to cats. Exemplary salts are monosodium phosphate and monocalcium phosphate.

U.S. Pat. No. 3,639,569 discloses the use of a tris(-phosphonoalkyl)amine in a dentifrice composition with a dentifrice abrasive selected from the group consisting of beta-phase calcium pyrophosphate, particulate thermosetting polymerized resin, alumina, sodium metaphosphate, and mixture thereof, or in a mouthwash composition, or in a chewing gum composition or dental prophylaxis paste composition. The patent discloses that the use of inorganic pyrophosphates as anti-calculus agents in oral compositions has the problem of hydrolysis in aqueous products and loss of activity prior to the termination of the normal shelf-life of such products. The patent also teaches that calculus inhibition by chelation of calcium ion may seriously damage tooth structure by decalcification.

U.S. Pat. No. 3,957,964 discloses microcapsules containing essential oils of mint flavor in a dentifrice adapted to release a plural flavor-burst signaling the onset of and the completion of a toothbrushing operation. The dentifrice may be a toothpaste having dicalcium phosphate as a polishing agent.

U.S. Pat. No. 3,959,458 discloses the use of from about 0.2 to about 8 percent by weight of an orally acceptable monofluorophosphate with an anticalculus agent which is a condensation product of ammonia and phosphorus pentoxide or with a polyphosphonate in an oral composition. The oral composition may further contain a calcium pyrophosphate abrasive. The patent teaches that sodium or calcium monofluorophosphate, when used in combination with the anticalculus agents, exhibit no detectable damage to silicate fillings in the mouth whereas other anticaries agents, such as sodium fluoride, do exhibit damage. It is also taught that below about pH 5.0 some of the anticalculus agents can damage dental enamel.

U.S. Pat. No. 4,314,990 discloses the use of a phosphate buffering agent, which provides phosphate ions to maintain the pH of a slurry in the range of about 6.8 to 8.0, in a toothpaste composition which comprises 6 to 45 percent of a silica dental abrasive, from about 0.01 to 3 percent of a fluoride ion source, from about 10 to 45 percent of water, and about 30 to 70 percent of a humectant.

U.S. Pat. No. 4,323,551 discloses the use of a tetraalkali metal pyrophosphate salt to provide from about 0.5 to 5 percent of the $P_2O_7^{-4}$ species in a mouthwash composition comprising 0.02 to 0.2 percent of a quaternary ammonium compound, and a carrier liquid wherein the pH is adjusted to about 7.0 to 9.5 with a mineral or organic acid.

U.S. Pat. No. 4,421,527 discloses the use of a precipitated amorphous silicon dioxide prepared by acidulation in an abrasive composition in a toothpaste that contains fluoride. Phosphoric acid is disclosed as an acidulant. Soluble phosphates, such as the pyrophosphates, are taught as improving fluoride pellicle penetration.

U.S Pat. No. 4,515,770 discloses a process wherein a soluble source of phosphate ions or a soluble source of calcium ions is uniformly distributed through sucrose in crystalline form as a result of dissolution of the sucrose and soluble source of calcium or phosphate ions in water followed by evaporation of the water solvent. It is taught that it is of substantial importance that the calcium or phosphate ion source be as rapidly soluble in saliva as the sugar so that the protective ions will migrate to salivary retention areas as rapidly as the sugar. A material, it is taught, which is cariogenic by virtue of directly or indirectly participating in the lowering of pH in salivary retention areas is rendered non-cariogenic by treatment to incorporate enough of either a calcium or phosphate ion source to keep the acidic medium from dissolving the tooth enamel. It is also disclosed that systematically administered phosphates are said to differ in cariostatic activity depending on the type of anion (cyclictrimeta-, hexameta-, ortho-, and pyrophosphate, increasing in effectivness in that order). It is further taught that these developments have unfortunately resulted in only minor advances in prevention of carious degradation of teeth because none of the "remineralization" processes have been shown to be consistently effective.

U.S. Pat. No. 4,515,772 discloses the use of from about 10 to about 70 percent of a dental abrasive selected from the group consisting of insoluble metaphosphates, alumina, thermosetting polymerized resins, and silica from about 50 to about 3,500 ppm of fluoride ions from a fluoride ion source, and an amount of a pyrophosphate salt selected from the group consisting of dialkali metal and mixtures of dialkali metal and tetraalkali metal pyrophosphate salts sufficient to provide at least 1.5 percent of $P_2O_7^{-4}$. The pyrophosphate ion is provided by a mixture of disodium pyrophosphate and tetrasodium pyrophosphate. The fluoride ion source is disclosed as an essential component. The upper limits on the sodium pyrophosphate salts are determined by solubility considerations, while the tetrapotassium level is established for taste reasons. It is further taught that surprisingly mixtures of certain pyrophosphate salts can provide a safe and effective anticalculus product while also not presenting difficult formulation problems.

U.S. Pat. No. 4,532,124 discloses the use of a plaque mineralizing aqueous solution comprising urea, a fluoride salt, a water-soluble calcium salt, and a water-soluble phosphate salt in the mineralization of dental plaque. It is disclosed that high plaque calcium and inorganic phosphate levels will lower the 'critical pH', that is, the pH which plaque must reach before it becomes unsaturated with respect to biological apatite, and enamel dissolution commences. The urea is metabolized by bacteria to produce alkali in plaque. Aspartame and amino acids may be substituted for the urea.

U.S. Pat. No. 4,540,584 discloses the use of coral sand as an effective component in a mineral supplement in an amount sufficient to provide calcium carbonate as a mineral supplemental for humans, such coral sand also containing $PO_4$. The composition is useful for replenishing calcium and phosphorous, as well as other minerals. Acidic foods tend to result in decayed teeth and bone fractures because of calcium poverty.

U.S. Pat. No. 3,567,459 discloses conversion of a hot melt of sugar having a moisture content less than 5 percent to a dough-like bone-forming composition by incorporation of nutritional fillers, fatty flavoring materials, and fat-absorbing farinaceous materials. The composition is formed and cooled. The patent teaches mastication of bones provides teeth cleaning benefits stemming from abrasion and other contacts of bone fragments.

U.S. Pat. No. 3,701,830 discloses the use of a neutral protease enzyme for removing plaque from and preventing the formation of calculus on the teeth of dogs wherein the neutral protease is obtained by fermentation with a strain of Bacillus suptilis or Bacillus sterothermophilus.

U.S. Pat. No. 3,882,257 discloses a process where 75 percent by weight of bones is admixed with 23.5 percent by weight of animal by-products, and the mixture is bound with salt in the preparation of a pet food having about 40 percent natural animal protein. The product enables a dog to exercise his jaws and gums to remove tartar from teeth.

U.S. Pat. No. 3,899,607 discloses a dough mixture which is: worked and shaped at a temperature of 170° to 220° F. to form a simulated bone having a structural matrix; or cooked, dried to a moisture content of between 5 and 12 percent by weight, ground and mixed with a dextrin adhesive to form a simulated bone having a structural matrix.

U.S. Pat. No 4,364,925 discloses that an enzyme for removing plaque and/or tartar from the teeth is included in a chew-resistant layer of an integral chew-resistant multi-layer animal food system having a structure supporting fibers. U.S. Pat. Nos. 3,194,738 and 3,686,393 also relate to the use of enzymes for inhibiting plaque.

U.S. Pat. No. 3,488,419 discloses the use of a polyphosphonate or salt thereof in compositions like dentrifices, mouthwashes, prophylaxis pastes and topical compositions. The patent teaches that inorganic polyphosphates, such as pyrophosphates, hydrolyze in aqueous products and do not remain in active form throughout the normal shelf-life of such products. Calculus and crystal growth inhibition tests on rats using calculus prophylaxis are disclosed. The patent also teaches that calculus inhibition by chelation of calcium ion may seriously damage tooth structure by decalcification.

U.S. Pat. No. 3,535,420 discloses the use of a cyclic tetraphosphonic acid as an anti-calculus agent in an oral composition. The patent teaches that inorganic polyphosphates, such as pyrophosphates, hydrolyze in aqueous products and do not remain in active form throughout the normal shelf-life of such products. It is also taught that although certain of the art-disclosed chelators are purportedly safe for use on dental enamel, the chemical similarity of calculus to the tooth structure limits the usefulness of the chelation approach because the more effective chelators can seriously damage the tooth structure by decalcification. The cyclic tetraphosphonates are calcium sequestrants, but they retard calculus formation by a mechanism that is believed to involve the inhibition of hydroxylapatite crystal growth rather than calcium sequestering.

U.S. Pat. No. 3,686,393 discloses the use of a dextranase used to eliminate dental plaque formation.

U.S Patent No. 3,956,479 discloses the use of a quaternary ammonium compound having a carbamate, or a thiocarbamate, or a dithiocarbamate, or a carbamide group in an oral preparation. The compounds are effective in reducing caries and inhibiting formation of oral calculus.

U.S. Pat. No. 4,003,971 discloses the use of a dentifrice component in the production of dentifrice speckles. Antimicrobial agents for incorporation into oral dentifrice formulations may be effective by reducing dental plaque or inhibiting the formation of dental calculus.

U.S. Pat. No. 4,254,101 discloses the use of from about 6 to 45 percent of a silica dental abrasive, from about 30 to 70 percent of a humectant, and from about 0.03 to 1.0 percent of a carboxyvinyl polymer in a toothpaste composition. The use of optional anticalculus agents in amounts of from about 0.01 to 2.5 percent by weight of the toothpaste composition are taught.

U.S. Pat. No. 4,472,373 discloses the use of a pyridium salt as an anti-plaque agent in a flavored alcoholic carrier. Phosphates, such as calcium pyrophosphate, are disclosed as dentifrice abrasives.

U.S. Pat. No. 4,153,732 discloses the use of at least one soluble aluminum ion containing salt with adipic acid, ascorbic acid, or mixtures thereof as a cariostatic additive for comestibles. The patent teaches that calcium pyrophosphate and insoluble sodium metaphosphate abrasives coact with aluminum fluoride in dentifrice compositions.

U.S. Pat. No. 4,627,977 discloses an oral composition, such as, a toothpaste (including gel or cream), mouthwash, lozenge, chewing gum or tooth powder, containing a calculus-inhibiting amount of a linear molecularly dehydrated polyphosphate salt (e.g., a water-soluble alkali metal pyrophosphate) to inhibit enzymatic hydrolysis of said polyphosphate salt in saliva, a combination of a fluoride ion-providing source and a synthetic linear polymeric polycarboxylate. See also British Published Patent Application No. 2,180,157.

U.S. Pat. No. 4,678,662 discloses calcium carbonate particles coated with at least one pyrophosphate derivative, such as, disodium dihydrogen pyrophosphate and tetrasodium pyrophosphate.

European Published Patent Application No. 0236920 discloses a dentifrice comprising essentially insoluble calcium pyrophosphate as an abrasive and a clinically effective amount of soluble pyrophosphate, such as, tetrasodium pyrophosphate, or tripolyphosphate as an anticalculus agent.

U.S. Pat. No. 4,684,518 discloses a process for reducing the incidence of calculus on dental enamel. The enamel surfaces in the mouth are contacted with a composition comprising a soluble pyrophosphate source capable of providing at least 1.5 percent of $P_2O_7^{-4}$ and from about 50 to about 3500 ppm of fluorine.

U.S. Pat. No. 4,722,461 discloses an oral composition in the form of a mouthwash or liquid dentifrice comprising: an amount of a fluoride ion source sufficient to supply from about 50 ppm to about 3500 ppm of fluoride ions; an amount of a pyrophosphate salt selected from the group consisting of dialkali metal and mixtures of dialkali metal and tetraalkali metal pyrophosphate salts sufficient to provide at least 1.5 percent of $P_2O_7^{-4}$; The pH of the composition is from about 6.0 to about 10.0. Calcium pyrophosphate is termed to be an abrasive. See European Published Patent Application No. 0097476.

British Published Patent Application No. 2,201,593 discloses an oral composition in the form of a toothpaste effective in reducing calculus comprising: a safe and effective amount of a soluble pyrophosphate salt or mixture of the salts; from about 5 to about 60 percent of a suitable toothpaste abrasive; an amount of a fluoride ion source sufficient to provide from about 50 ppm to about 3500 ppm fluoride; from about 5 to about 60 percent of humectant selected from the group consisting of sorbitol, glycerine, polyethylene glycols, mineral oil, and mixtures thereof; from about 0.3 to about 5 percent of a surfactant selected from the group consisting of alkyl sulfate surfactants, ethoxylated alkyl sulfate surfactants and mixtures thereof; and water. The composition has a pH of from about 6 to about 10, is substantially free of polyethylene glycols having fewer than six ethoxy units and short chain monohydric alcohols and has potassium ions present at a level of from about 0.5 to about 7 percent. The soluble pyrophosphate salt can be, for example tetrapotassium pyrophosphate, tetrasodium pyrophosphate, sodium acid pyrophosphate and mixtures thereof.

U.S. Pat. No. 4,806,340 discloses an oral dentifrice composition such as a toothpaste, dental gel, toothpowder, dental tablet or lozenge containing as anticalculus agent about 4.3 to about 7 percent of alkali metal pyrophosphates comprising at least 4.3 percent of tetrapotassium pyrophosphate alone or admixed with up to 2.7 percent of tetrasodium pyrophosphate, and as inhibitors against enzymatic hydrolysis of such agent in saliva, a fluoride and preferably up to about 3 percent of a synthetic anionic polymeric polycarboxylate. The composition is used in a program of oral hygiene and/or for inhibiting dental calculus. It is known that saliva contains acid phosphatase, alkaline phosphatase and pyrophosphatase enzymes. It is considered that any one of the three enzymes may adversely affect pyrophosphates as an inhibitor of hydroxyapatite formation and calculus. It is accordingly apparent that an anticalculus pyrophosphate dentifrice composition, should inhibit, reduce or nullify the destructive activity of all three salivary enzymes. See Also British Published Patent Application No. 2,182,244.

Australian Published Patent Application No. 168071 discloses a dialkali metal-alkaline earth metal pyrophosphate containing about 1 to about 5 percent by weight of chemically combined fluorine. The composition is a dentifrice base. The method of producing the fluorinated dialkali metal-alkaline earth metal pyrophosphate, which comprises reacting together, in the presence of an aqueous medium, a water-soluble metal fluoride, an alkali metal pyrophosphate (such as, tetrasodium pyrophosphate), and a water soluble alkaline earth metal salt. The reactants being employed in the proportions required to yield a dialkali metal-alkaline earth metal pyrophosphate containing about 1 to about 5 percent by weight of chemically combined fluorine.

British Patent No. 777,556 discloses a dentifrice composition which contains a fluoride compound which releases fluoride ions in water, a calcium polyphosphate polishing agent, and a calcium ion suppression agent to maintain the effect of the fluoride upon ageing.

BROAD DESCRIPTION OF THE INVENTION

An object of the invention is to provide raw hide having a coating containing pyrophosphate, particularly in strip form. Another object of the invention is to provide a process for preparing raw hide , particularly in strip form, having a coating containing pyrophosphate. Another object of the invention is to provide a process for the prevention of tartar accumulation on the teeth of dogs. A further object of the invention is to provide a process for the prevention of tartar accumulation on the teeth of dogs by the chewing and eating of raw hide, particularly in strip form, having a coating containing pyrophosphate by the dogs. Another object is to provide a coating for human or animal baked dough products.

Other objects and advantages of the invention are set out herein or are obvious herefrom to one skilled in the art.

The objects and advantages of the invention are achieved by the compositions and process of the invention.

The invention includes a process for preparing raw hide having a coating containing at least one inorganic pyrophosphate compound, comprising:
(a) subjecting raw hide to a liquefied coating material at least one inorganic pyrophosphate compound; thereby, forming a coating of such liquefied coating material on the raw hide; and
(b) drying the raw hide having a coating containing said at least one inorganic pyrophosphate compound.

The invention further includes raw hide having a coating containing at least one inorganic pyrophosphate salt. The invention also includes a process for the prevention of tartar accumulation on the teeth of dogs comprising chewing and/or eating the raw hide having a coating containing at least one inorganic pyrophosphate.

Tartar is an incrustation on the teeth consisting of salivary secretion, food residue and various salts, such as, calcium carbonate or phosphate. Tartar is also termed dental calculus.

Caries are cavities or decay of the teeth which begins at the surface of the tooth and may progress through the dentine into the pulp cavity. It is believed that the action of microorganisms in the mouth on ingested sugars and carbohydrates produces acids that eat away the enamel. By preventing the formation of calculus or tartar, the invention formulation is in effect an anti-cariogenic agent.

In the preparation of raw hide, the skin that is made into raw hide should not be salted: Instead, it is softened with water and immersed in a dehairing solution made, for example, by combining 2½ pounds of slaked caustic lime with ten gallons of water. The skin is left in the solution until the hair slips very easily, and then it is removed and rinsed in clean water. After letting the skin drain, it is put on the fleshing beam and the hair is scraped off as well as the epidermis layer of skin under the hair. When the hair is gone, the hide is turned over and fleshed very well, removing every bit of flesh and fat. Then the hide is soaked for a while in clean water to wash away all dirt and bits of material removed by the fleshing and dehairing operations. The hide is stretched on a frame and allowed to air dry.

More generally, hair removal can be accomplished with a saturated solution of calcium hydroxide (lime) alone or in combination with a sharpening agent, e.g., sodium sulfide or sodium sulfhydrate. Lime by itself does not dissolve the hair but only loosens it in the base of the hair follicle for easy removal by an unhairing machine. This labor-intensive apparatus scrapes the loosened hair from the surface of the skin and is termed a hair-save process. Lime, by itself, requires from 5 to 7 days to loosen the hair. Because of the importance of time, a hair-burn process is more commonly used. Although sulfide at a pH greater than 11.5 can dissolve the hair in as little as 30 to 40 minutes, the usual sulfide unhairing process takes from 4 to 6 hours.

The dehairing scheme using ultrasonic vibration of U.S. Patent No. 2,965,435 can be used.

The relatively brief unhairing step can be followed by the longer (4 to 16 hours) liming step. The spent unhairing liquors with the dissolved hair are drained from the hides and a fresh saturated lime solution is added. The action of lime not only loosens the hair but opens up the collagen fiber structure. Collagen swells outside of its isoelectric point in either acid or base in 8 to 48 hours. This swelling leads to subsequent fiber separation. (When the invention liquefied coating material is subsequently applied to the raw hide, its consistency, viscosity, solids content, etc., keeps it primarily on the surface of the raw hide. Some of the liquefied coating material will seep into the surface regions of the raw hide, thereby, helping to anchor or adhere the coating to the raw hide once it is dried.)

The liming step, when complete, is followed by a deliming. The hide is washed to remove soluble lime and hair particles. At this point, the stock is at a pH of 12.5. The most widely used deliming salt is ammonium sulfate, which lowers the pH to 8 to 9.

Puering is the treatment of delimed or partially delimed skins. Bating is a similar process, generally 'synthetic' bates are used; these contain enzymes, obtained from the pancreas of animals, to which neutral deliming salts are added. Puering and bating assist in the removal of short hairs, lime soaps, and cementing substances in the skin, and in depleting and deliming. As a result of this process, the stretch and pliability of the leather is increased. Puering and bating are optional in the process of preparing edible raw hide for dogs and other animals.

The invention product is dried so that it comprises a dry raw hide strip having at least one inorganic pyrophosphate.

Dogs prefer the coated product over uncoated raw hide, but then go on to eat the uncoated product. Various coatings apparently are an individual dogs' preference. Dogs appear to attempt to gnaw the coating off of the coated raw hide after the initial smell and taste. After the coating is gone sometimes the raw hide is left uneaten. The invention product is very effective in reducing the accumulation of tartar on the teeth of dogs.

The invention product should be slightly acid to near neutral.

The invention product is chewable, tough and flexible. When chewed by dogs, the invention product cleans teeth surfaces, removes tartar (by mechanical action), and exercises and massages the gums. The pyrophosphate in the invention prevents the formation of tartar on the dog's teeth.

The inorganic pyrophosphates are anti-tartar, anti-plaque or anti-calculus agents. The invention product exhibits anti-tartar properties over its normal shelf-life. The invention product does not adversely affect canine tooth enamel.

The invention further includes a coating comprised of malto-dextrin, food starch or modified food starch, optional colorant, optional flavorant for animals or humans suitable polysaccharide gum (preferably xanthan gum), surfactant (preferably lecithin or modified lecithin), vegetable fat or animal fat). The coating can be used on baked dough products, such as, baked dog biscuits.

DETAILED DESCRIPTION OF THE INVENTION

As used herein, all parts, percentages, ratios and proportions are on a weight basis unless otherwise stated herein or otherwise obvious herefrom to one skilled in the art. As used herein, all temperatures are in degrees Fahrenheit unless otherwise stated herein or otherwise obvious herefrom to one skilled in the art.

Hides are normally prefleshed to remove excess flesh before shipping to companies that prepare raw hide therefrom. If the hides have been pre-soaked in salt, the salt can be removed by conventional methods.

Air drying is satisfactory for hides, but it must not be too slow or putrefaction may begin. If the air drying is too fast, the outer surface may become hard and dry while the inner parts still have enough moisture to support bacterial growth. Fresh hides, if immediately removed from the animal, can be chilled and washed to remove any excess manure and then sprayed with a disinfectant. The longer the period of time the disinfectant is effective the longer it will be before there is any damage to the hides and the greater the distance that the hides can be shipped. One should make sure that the disinfectant is removed before or during the dehairing and/or liming step.

The raw hide is preferably made from cattle hides, but can be made from horse hides, calf skins, sheep skins, goat skins, kid skins, marsupial skins, buffalo hides and pig skins, for example. Fresh cattle hides contain 65 to 70 percent of water, 30 to 35 percent of dry substance, and less than 1 percent of ash. The dry substance is largely made up of the fibrous proteins, collagen, keratin, elastin, and reticulin. The main components of the ash, listed in decreasing concentration, are phosphorus, potassium, sodium, arsenic, magnesium, and calcium.

Collagen in the hides is responsible for the toughness and strength in the raw hide.

Liming is a process in which the hides or skins are immersed in solutions of milk of lime, or slaked lime, to which small amounts of sodium sulphide, ammonium salts, or sometimes enzymes may be added. The object of liming is primarily to loosen the hair, usually by destroying or loosening the epidermis: at the same time the fibrous structure becomes swollen and plumped with a partial separation of the fibres. Lime and other alkalis combine with the natural grease in the skin to form soaps, which are removed in the subsequent bating and scudding operations. Liming may be carried out by immersing the pelts in pits, paddles, or drums.

In pit liming the hides or skins are placed in brick or concrete pits. The goods are immersed in lime liquor in the pits for three days, after which time either the liquor is strengthened by the addition of freshly slaked lime paste (one pit system), or the goods are transferred to a once-used lime liquor and after a further three days placed in a new liquor (three pit system), the total period being 8 to 10 days. Pit liming is laborious as the goods must be hauled frequently from the pits to permit circulation of the liquor. Mechanical devices have been devised for agitating lime liquors but have not met with general acceptance. Instead of using pits, liming in a drum is more generally favored since it reduces both time and labor.

Unhairing or dehairing is a process in which the hair is removed from the skin after it has been loosened by liming. This may be done manually by means of a bluntedged knife which is tilted away from the operator, so that the hair and scud are pushed or scraped off the skin. Unhairing machines, in which the hair side of the skins is brought near to a rapidly revolving cylinder fitted with a series of blunt blades, have largely superseded hand unhairing.

Any adipose tissue remaining on the flesh side of the skin is removed, after liming, in the process of 'fleshing'. A special knife is used for hand flashing, but the process is usually carried out by means of a fleshing machine comprising a revolving roller fitted with sharp spiral blades.

The deliming is preferably complete. Unless the lime is removed, the finished leather is hard with a brittle grain and shows discolorations. Only about 50 percent of the lime can be removed from the skin by washing in running water, the residual lime being combined with some of the free acid groups in the collagen. By treatment with inorganic acids, organic acids, or acid salts complete removal of lime is effected.

The hides, skins, or leather are often separated or split into two sections or layers of even thickness; the outer or grain layer, and the under or flesh layer. The splitting is usually done on a band knife splitting machine.

The prepared raw hides can be cut into strips by a cutter that exerts a scissor-like action.

The solvent used in the coating is preferably water, but other non-toxic, edible solvents, such as, ethanol or ethanol/water, can be used. The problem of the necessity of solvent removal from the treated raw hide due to toxicity is to be avoided in most cases. If a mixture of ethanol and water is used, the amount of ethanol in the mixture is generally about 5 to about 60 percent, preferably about 5 to about 25 percent. When one or more of the inorganic pyrophosphates is not water soluble, it may be ethanol soluble.

The invention includes the use of at least one inorganic pyrophosphate. Preferably the inorganic pyrophosphates are water soluble. A water insoluble inorganic pyrophosphate(s) can be used by itself or in a mixture with at least one water soluble inorganic pyrophosphate. Water insoluble ingredients result in a slurry. The use of very fine particles of a water insoluble inorganic pyrophosphate provides better suspension in the coating formulation. Water insoluble inorganic pyrophosphates have abrasive action.

The inorganic pyrophosphates are preferably alkali metal pyrophosphates. The preferred alkali metal pyrophosphates are tetrasodium pyrophosphate and tetrapotassium pyrophosphate. An examples of a useful tetraalkali metal pyrophosphate is tetralithium pyrophosphate. Alkaline earth metal pyrophosphates are also useful, but they are generally insoluble in water. Preferably the inorganic pyrophosphates are soluble in water.

Kirk + Othmer, "Encyclopedia Of Chemical Technology", 2nd Ed., Vol. 15, (1965), pages 232 to 276, discloses a number of water-soluble and water insoluble inorganic pyrophosphate salts. The pertinent portions of Kirk + Othmer, "Encyclopedia Of Chemical Technology", 2nd Ed., Vol. 15, (1965), pages 232 to 276, are incorporated herein by reference.

Examples of dialkaline metal pyrophosphates are dicalcium pyrophosphate, dibarium pyrophosphate, and dimagnesium pyrophosphate. Trialkali metal monoacid pyrophosphates, such as, trisodium hydrogen pyrophosphate, can be used. Monoalkali metal triacid pyrophosphates, such as, sodium trihydrogen pyrophosphate, can also be present in limited amounts. Examples of other inorganic pyrophosphates include dimanganese pyrophosphate and dizinc pyrophosphate.

The formula $M_{n+2}P_nO_{3n+1}$, where M is a univalent metal, is the formula for univalent metal pyrophosphates when n is 2. The formula $M_{n+2}P_nO_{3n+1}$, where M' is a divalent metal, is the formula for divalent metal pyrophosphates when n is 2. Such univalent metal pyrophosphates and divalent metal pyrophosphates can be used in the invention. Polyphosphates have the formula $M_{n+2}P_nO_{3n+1}$, or $M'_{n+2}P_nO_{3n+1}$, where n is 2,3,4,5, ..., and the oxide ratio R between the cationic oxides and anionic oxides ($P_2O_5$) is between 1 and 2. The oxide ratio for pyrophosphate is 2.

Tetrasodium pyrophosphate, one part, is soluble in 13 parts of cold water and in 2.5 parts of boiling water. It is insoluble in ethanol. Dicalcium pyrophosphate is practically insoluble in water. The invention use of the term "solution" includes slurries, suspensions and the like. Tetrapotassium pyrophosphate is freely soluble in water and is insoluble in ethanol.

The invention product does not include any fluorine-containing compound or other fluoride ion source, or quaternary ammonium compounds.

The invention does not include organic acid pyrophosphates.

Preferably a mixture of trisodium monoacid pyrophosphate and tetrapotassium pyrophosphate is used (in a ratio to achieve the desired pH).

Federal GRAS regulations are that the upper amount of pyrophosphate moiety, $P_2O_7$, delivered is 0.5 weight percent (based on the total composition). The maximum allowable GRAS level in a composition for sodium acid pyrophosphate (SAPP) is 0.3 weight percent and tetrasodium pyrophosphate (TSPP) is 0.5 weight percent, such weight percentages being based on the total weight of the product.

The preferred invention solution contains trisodium monoacid pyrophosphate (SAPP) and tetrapotassium pyrophosphate in a weight ratio of about 60 to about 40.

The pyrophosphate(s) is used in sufficient amount to deliver generally from about 0.1 to about 5, preferably from 0.4 to 0.5 weight percent (based on the total composition) of $P_2O_7$.

A study of the application of aqueous solutions of a mixture of tetrasodium pyrophosphate and sodium acid pyrophosphate to the teeth of dogs by spraying for one month resulted in dose response data. The aqueous solutions containing 5 and 3 weight percent of such pyrophosphate mixture resulted in significant reductions in tartar accumulation. The aqueous solutions containing 1.5 and 0.5 weight percent resulted of such pyrophosphate mixture in directional trends of reductions in tartar accumulation.

The ratio of sodium acid pyrophosphate (SAPP) to tetrapotassium pyrophosphate (TKPP) is between 0.01 to 99.99 weight percent and 99.99 to 0.01 weight percent.

The pH of the solution of at least one inorganic pyrophosphate compound (salt) is generally in the range of about 4 to about 10.5, typically from about 5 to about 8, preferably from about 5.5 to about 6.5, most preferably about 6.

The solution application is usually conducted at a temperature of about 45° to about 200° F., preferably about 60° to about 190° F.

The solution can also contain suitable surfactants or emulsifying agents. The preferred surfactant is lecithin or a modified lecithin, most preferably a modified lecithin which is in a dry form. Preferably about 0.5 to about 1.75 weight percent of the lecithin or modified lecithin is used. The surfactant or wetting agent helps the coating material to apply over the entire surface of the raw hide strips.

The liquefied coating formulation best contains at least one suspension agent. The preferred suspension agent is a polysaccharide gum. Preferably about 0.05 to 1.25 weight percent of xanthan gum is used. Xanthan gum is one of the few gums which acts as an acceptable suspension agent in the invention. Other suitable gums and mucilages can be used. Xanthan gum is preferred because it is stable over a broad range of temperature and holds the same viscosity in the liquefied coating formulation over the broad temperature range. The xanthan gum has a bodying effect so that little or no separation occurs.

Malto-dextrin produced by hydrolyzing corn starch is preferred. It serves as a carrier (bodying), binding agent and suspension agent and helps the appearance of the coating. Other malto-dextrins can also be used for the same functions.

An adhesive or binding agent, such as, malto-dextrins, is needed in the coating slurry to help the coating material bind (adhere) to the raw hide when the raw hide is dipped in the coating slurry. Preferably about 5 to about 15 weight percent of the malto-dextrin is included in the coating material.

A carrier, such as, starch or a modified food starch, is included in the coating formulation. Preferably about 0.1 to about 5 weight percent of the food starch or modified food starch is included in the coating material. The food starch or modified food starch also serves to control the viscosity.

Animal fat preferably is included for flavor purposes. Other suitable flavorants can be included, particularly salt. The flavorants can be any dairy product flavorant, such as, milk or cheese, meat flavorants, such as, liver or beef, poultry and fish. Flavorants help provide palatability for the invention coating.

Preferably a hydrogenated vegetable oil, is included in the coating formulation for sheen and to modify the melting point of the formula fats in the finished product. It also helps to prevent flaking of the coating; also the coating does not have a tacky feeling.

Any suitable colorant can be included in the coating formulation. The preferred colorant is caramel color, which also provides some flavor to the product.

The coating also incorporates sufficient water to achieve the liquefied coating composition. Amounts of other ingredients are those which are effective to achieve their functions in the coating formulation.

The preferred coating formulation, besides the inorganic pyrophosphates, contains animal fat, a surfactant, such as, a modified lethicin, polysaccharide gum, a modified food starch, flavorant, colorant, hydrogenated vegetable oil, and a carrier, such as malto-dextrin and water.

The coating formulation should be viscous enough so that the coating formulation generally only coats the surface regions of the raw hide. The presence of coating in the surface regions of the raw hide helps to anchor the resultant coating and to prevent the coating from easily being separated from the raw hide during handling and shipping and also by the chewing action of the dog. Basically, though, the coating is strictly a surface phenomena on the raw hide.

The coating slurry can be applied to the raw hide by any suitable means, such as, spraying, soaking in a container, etc., but the preferred method is by dipping the raw hide strips in the solution. (The raw hide could be in long rope form; the coating applied and dried; and the rope then cut into shorter strips.) The coating slurry is applied generally at a temperature of 45° to 200° F., preferably at about 60° to about 190° F., and most preferably at about 180°. The coating slurry has a low microbial profile at such higher temperatures.

After treating the raw hide with the pyrophosphate compound slurry, the raw hide is dried. While the treated raw hide is preferably air dried, it is also advantageous to dry the treated raw hide using applied heat, e.g., in a hot air oven (at a temperature of say 75° to 300° F.).

The invention product can be raw hide in any shape which can be chewed by dogs. Examples of such raw hide shapes are strips, balls made up of pieces or strips, knotted strips, bones made up of pieces or strips, curled pieces, etc. The raw hide can be that which has been molded (e.g., compressed, extruded, stamped, tabletted, etc.) and formed.

The invention deals primarily with dogs, but has a scope of teeth bearing non-human animals or mammals, such as, cats. The invention composition is used to reduce or prevent tartar accumulation on canine teeth and other non-human animal or mammal teeth.

The preferred coating formulation is:

TABLE 1

| Ingredients | Percentages | |
|---|---|---|
| | Specific | Ranges |
| Sodium acid pyrophosphate (SAPP), anhydrous powder, (non-leavening type) | 1.73 | 0.25-5 |
| Tetrapotassium pyrophosphate (TKPP), anhydrous powder | 1.15 | 0.25-5 |
| Salt | 0.50 | 0.05-2.5 |
| Melto-dextrin | 9.17 | 2-30 |
| Food starch-modified | 2.00 | 0.1-10 |
| Colorant | 0.50 | 0.01-3 |
| Flavorant | 2.00 | 0.01-5 |
| Xanthan | 0.20 | 0.05-1.5 |
| Lecithin or modified lecithin | 1.25 | 0.5-1.75 |
| Vegetable fat | 0.50 | 0.1-3 |
| Animal Fat | 1.00 | 0.1-5 |
| Subtotal | 20.00 | |
| Water | 80.00 | 50-97 |
| Total | 100.00 | |

Definitions and trade name materials:
SAPP is trisodium acid pyrophosphate (or sodium pyrophosphate).
TSPP is tetrasodium pyrophosphate.
TKPP is tetrapotassium pyrophosphate.

EXAMPLES 1 to 17

In the examples, the following procedure was used. The coated raw hide strips were prepared by:
(a) blending the dry powders.
(b) adding ¼ of the water and slurring the composition.
(c) adding remaining ¾ of water and mixing to form the coating formulation.
(d) heating the coating formulation to 185° F. to 200° F. with intermittent stirring (add animal fat at about 125° F. during the heating).
(e) maintaining the coating formulation at 160° to 190° F.
(f) immersing raw hide strips by dipping in the heated coating formulation and holding the raw hide strips to the edge to let drain for about 15 seconds.

(g) placing the coated raw hide strips on a screen and drying at 275° F. for 7 minutes in a forced-air laboratory oven.

(h) let the raw hide strips cool and then package them. Any deviations from such procedure is set out in the specific examples.

The raw hide strips had a calculated average weight of 17 grams each, although actual weight ranged from 8.5 to 335 grams.

The specific ingredients, conditions, etc., are set out in the following tables:

TABLE 2

| Ingredients, Percentages by weight | Examples | | | |
|---|---|---|---|---|
| | 1 | 2 | 3 | 4 |
| SAPP | | 3.4 | 3.4 | 3.4 |
| TSPP | | 2.3 | 2.3 | 2.3 |
| Malto-dextrin A | 10.0 | 10.0 | | 5.0 |
| Malto-dextrin B | | | 5.0 | |
| Food starch modified | | | 5.0 | |
| Colorant | 0.5 | 0.5 | 0.5 | 0.5 |
| Flavorant | 1.0 | 1.0 | 1.0 | 1.0 |
| Xanthan gum | 1.0 | 1.0 | 1.0 | 1.0 |
| Gelatin, | | | | 6.0 |
| Water | 87.5 | 81.8 | 81.8 | 81.8 |
| Heated coating to 180° F. | yes | yes | yes | yes |
| pH of mixture at 160° F. | 6.4 | 5.97 | 5.87 | 5.8 |
| Raw hide dry only weight | 13.811 | 24.962 | 14.705 | 11.289 |
| | 24.655 | 23.957 | 9.485 | 17.936 |
| Raw hide wet weight | | 28.650 | 21.480 | 13.399 |
| | | 33.840 | 27.280 | 20.420 |
| Dried at 200° F. for: | 15 min. | 10 min. | 15 min. | 10 min. |
| Raw hide dry weight | | 25.977 | 16.738 | 11.782 |
| | | 27.348 | 24.825 | 18.546 |

Notes: 1. The pH of the water was 8.0.
Comments:
In Example 1, the coating was thick, had a nice appearance and had a weight pick up of 2.7 g.
In Example 2, the coating was very thin, had a blotchy appearance and did not adhere evenly on the raw hide.
In Example 3, the coating was thick and had a nice appearance.
In Example 4, the coating was thin and had a blotchy appearance.

TABLE 3

| Ingredients, Parts by weight | Examples | | |
|---|---|---|---|
| | 5 | 6 | 7 |
| SAPP | 3.2 | 3.2 | 3.2 |
| TSPP | 2.13 | 2.13 | 2.13 |
| Malto-dextrin B | 10 | 10 | 10 |
| Modified Food Starch | 2.0 | 2.0 | 2.0 |
| Cereal | 0.5 | 0.5 | 0.5 |
| Flavorant | 1.0 | 1.0 | 1.0 |
| Xanthan gum | 0.2 | 0.2 | 0.2 |
| Modified lecithin | | 1.0 | |
| Animal fat | | | 2.0 |
| Water | 81.0 | 80.0 | 79.0 |
| pH at 160° F. (coating) | 5.9 | 5.9 | 5.9 |
| Raw hide dry only weight | 18.171 | 18.843 | 18.017 |
| | 14.346 | 23.897 | 16.046 |
| Raw hide wet weight | 20.340 | 21.300 | 20.070 |
| | 16.730 | 26.660 | 18.020 |
| Dried at 200°–225° F. | 15 min. | 15 min. | 15 min. |
| Raw hide (finished) dry weight | 18.613 | 19.432 | 18.323 |
| | 14.553 | 24.484 | 16.265 |

Notes: 1. The pH of the water was 8.3.
Comments:
In Example 5, the coating had a blotchy appearance.
In Example 6, the coating was considered best of Examples 5 to 7, had an even distribution appearance and was complete.
In Example 7, the coating again had a blotchy appearance.

TABLE 4

| Ingredients, Parts by weight | Examples | | | | |
|---|---|---|---|---|---|
| | 8 | 9 | 10 | 11 | 12 |
| SAPP | 1.73 | 1.73 | 1.73 | 1.73 | 1.73 |
| TSPP | 1.15 | 1.15 | 1.15 | 1.15 | 1.15 |
| Malto-dextrin B | 11.00 | 11.00 | 12.0 | 11.0 | 9.67 |
| Modified Food Starch | 2.0 | 2.0 | | 1.5 | 2.0 |
| Colorant | 0.5 | 0.5 | 0.5 | 0.5 | 0.5 |
| Flavorant | 2.42 | 2.42 | 2.42 | 2.42 | 2.0 |
| Xanthan gum | 0.2 | 0.2 | 0.2 | 0.2 | 0.2 |
| Modified lecithgran | 1.0 | 1.0 | 1.0 | 1.5 | 1.25 |
| Vegetable fat | | 1.0 | 0.9 | | 0.5 |
| Animal fat | | | | | 1.0 |
| Water | 80.0 | 79 | 80 | 80 | 80 |
| Heated coating form. to 180° F. | yes | yes | yes | yes | yes |
| pH of mixture at 160° F. | 5.9 | 5.9 | 6.0 | 6.0 | 6.0 |
| Raw hide dry only weight | 18.082 | 16.928 | 12.983 | 12.217 | 15.917 |
| | 15.247 | 15.037 | 15.077 | 15.304 | 12.073 |
| Raw hide wet weight | 21.189 | 14.690 | 15.930 | 15.130 | 19.160 |
| | 18.575 | 18.310 | 18.000 | 18.370 | 14.178 |
| Dried at 225° F. for: | 15 min. | 15 min. | 15 min. | 15 min. | 15 min. |
| Raw hide dry weight | 18.846 | 12.472 | 13.621 | 12.776 | 16.590 |
| | 15.987 | 15.688 | 15.588 | 15.947 | 12.586 |

Notes:
1. The pH of the water was 8.2.
2. Drying at 350° and 325° F. for 5 minutes curled the raw hide. It was satisfactory to dry at 300° F. for 7 minutes.
Comments:
In Example 8, the coating had a good appearance.
In Example 9, the coating was better than that of Example 10 and similar to that of Example 8.
In Example 10, the coating was satisfactory.
In Example 11, the coating was similar to those of Examples 8 and 9 and was better than that of Example 10.
Example 12, best of all results.

TABLE 5

| Ingredients, parts by weight | Examples | | | | |
|---|---|---|---|---|---|
| | 13 | 14 | 15 | 16 | 17 |
| SAPP | 1.73 | 1.73 | | 1.73 | 1.73 |
| TKPP | 1.15 | 1.15 | | 1.15 | 1.15 |
| Salt | 0.5 | 0.5 | 0.5 | 0.5 | 0.5 |
| Malto-dextrin B | 9.17 | 9.5 | 10.05 | 8.73 | 8.81 |
| Modified Food Starch | 2.0 | 2.0 | 2.0 | 2.0 | 2.0 |
| Colorant | 0.5 | | 0.5 | 0.5 | 0.5 |
| Flavorant | 2.0 | 2.17 | 2.0 | 2.0 | 2.0 |
| Xanthan Gum | 0.2 | 0.2 | 0.2 | 0.2 | 0.2 |
| Modified lecithgran | 1.25 | 1.25 | 1.25 | 1.25 | 1.25 |
| Vegetable fat | 0.5 | 0.5 | 0.5 | 0.5 | 0.5 |
| Animal fat | 1.0 | 1.0 | 1.0 | 1.0 | 1.0 |
| Sodium bicarbonate | | | | 1.44 | 0.36 |
| Water | 80 | 80 | 82.0 | 79.0 | 80.0 |
| Heated coating to 180° F. | yes | yes | yes | yes | yes |
| pH of mixture at 160° F. | 5.8–6 | 5.8 | 5.7 | 7.5 | |
| Raw hide dry weight | 20.867 | 32.990 | 19.134 | 16.634 | 12.680 |
| | 23.233 | 24.136 | 13.786 | 11.883 | 11.987 |
| Raw hide wet Weight | 24.140 | 36.610 | 22.150 | 19.040 | |
| | 26.290 | 27.580 | 15.900 | 14.140 | |
| Dried at 300° F. | 7 min. | 7 min. | 7 min. | 7 min. | 7 min. |
| Raw hide dry Weight | 21.720 | 34.056 | 19.803 | 17.025 | |

TABLE 5-continued

| Ingredients, parts by weight | Examples | | | | |
|---|---|---|---|---|---|
| | 13 | 14 | 15 | 16 | 17 |
| | | | | 23.907 | 25.015 |

Notes:
1. The pH of the water was 8.
2. The treated raw hide strips had an average weight of 20.18 g, the untreated raw hide strips had an average weight of 18.92 g, and the average weight pickup was 1.25 g.

Comments:
In Example 13, the coating was a good one.
In Example 14, the coating was a good one but had no color in the formula.
In Example 15, the coating was a good one.
In Example 16, the coating formulation had good dispersion but there was excessive foaming.
In Example 17, there was less foaming but did not aid dispersion.

Definitions:
SAPP is sodium acid pyrophosphate.
TSPP is tetrasodium pyrophosphate.
TKPP is tetrapotassium pyrophosphate.

The invention includes a viscous, liquefied coating formulation comprised of a surfactant, an effective polysaccharide gum, a binding agent, a starch carrier, a hydrogenated vegetable oil. A preferred coating formulation contains a surfactant, such as, lecithin or modified lecithin, xanthan gum (or other suitable polysaccharide gum), a starch or modified food starch, hydrogenated vegetable oil and a binding agent, such as, malto-dextrin, and water. Optional ingredients include animal fat, flavorant and colorant. A suitable humectant, preferably propylene glycol, can be used in the coating formulation. The invention coating can, but does not have to, contain at least one inorganic pyrophosphate salt.

The invention coating can be applied to any suitable human or animal food, such as, non-human animals, e.g., cats and dogs. The invention coating is preferably applied to baked dog biscuits and then both are dried.

The liquefied coating formulation best contains at least one suspension agent. The preferred suspension agent is a polysaccharide gum, most preferably xanthan gum. Preferably about 0.05 to 1.25 weight percent of polysaccharide gum (xanthan gum) is used. Xanthan gum is one of the few gums which acts as an acceptable suspension agent in the invention. The xanthan gum is an excellent agent for controlling the bodying effect, as it is stable over a broad temperature range, i.e., it holds the same viscosity over a large temperature range without any separation of the coating ingredients. Other suitable gums and mucilages can be used.

Malto-dextrin produced by hydrolyzing corn starch is preferred; it serves as a carrier (bodying), binding agent and suspension agent and helps the appearance of the coating; and it is a preferred ingredient. Other malto-dextrins can also be used.

An adhesive or binding agent, such as, malto-dextrins, is needed in the coating slurry to help the coating material bind (adhere) to the raw hide when the raw hide is dipped in the coating slurry. Preferably about 5 to about 15 weight percent of the malto-dextrin is included in the coating material.

A carrier, such as, starch or a modified food starch, is included in the coating formulation. Preferably about 0.1 to about 5 weight percent of the food starch or modified food starch is included in the coating material. The food starch or modified food starch also serves to control the viscosity.

Animal fat preferably is included for flavor purposes.
Other suitable flavorants can be used or included, particularly salt. The flavorants can be any dairy product flavorant, such as milk or cheese, meat flavorants, such as, liver or beef, poultry and fish. Flavorants help provide palatability for the invention coating.

Preferably a hydrogenated vegetable oil is included in the coating formulation for sheen and to modify the melting point of the formula fats in the finished product. It also helps to prevent flaking of the coating; also the coating does not have a tacky feeling.

Any suitable colorant can be included in the coating formulation. The preferred is caramel color which also provides some flavor to the product.

The coating also incorporates sufficient water to achieve the liquefied coating composition. Amounts of the other ingredients are those which are effective to achieve their functions in the coating formulation.

A preferred coating formulation for dog biscuits contain water, animal fat, a surfactant, such as, a modified lecithin, xanthan gum, a modified food starch, flavorant, colorant, hydrogenated vegetable oil and a carrier, such as a malto-dextrin.

Another preferred embodiment for the invention coating for dog biscuits and ranges of the ingredients of the coating is:

| Ingredients | Percentages | |
|---|---|---|
| | Specific | Ranges |
| Salt | .50 | .05-2.5 |
| Malto-dextrin | 9.17 | 2-30 |
| Food starch modified | 2 | .1-10 |
| Colorant | .50 | .01-3 |
| Flavorant | 2 | .01-5 |
| Xanthan gum | .20 | .05-1.5 |
| Lecithin or modified lecithin | 1.25 | .5-1.75 |
| Vegetable fat | .50 | .1-3 |
| Animal Fat | 1 | .1-5 |
| Subtotal | 17.12 | |
| Water | 82.88 | 50-about 97 |
| Total | 100.00 | |

The invention coating formulation can contain a humectant, such as, corn syrup, sugar and polyalcohols, such as, propylene glycol (preferred), sorbitol and glycerin.

The invention product does not include any fluorine-containing compound or other fluoride ion source, or quaternary ammonium compounds.

The invention coating can be applied, for example, to any suitable dog food, such as, dog biscuits, which can be made from any suitable dog food dough, such as, suitable dog biscuit dough. Any suitable dough comprising at least one flour, meal, fat and water can be employed for the product. For instance, when the desired product is a canine biscuit, a conventional dough for dog biscuits can be used, optionally containing discrete particles of meat and/or meat by products or farinaceous material. Such doughs typically contain fat solids. Examples of suitable doughs for the production of hard dog biscuits are disclosed in U.S. Pat. No. 4,454,163, and suitable doughs for the production of soft dog biscuits (containing humectant to control water activity) are disclosed in U.S. Pat. No. 4,454,164. The pertinent portions of U.S. Pat. Nos. 4,454,163 and 4,454,164 are incorporated herein by reference. Particulate proteinaceous particles, such as particles of meat, texturized vegetable protein and/or meat byproducts can be incorporated to add flavor to the biscuits and texturize the surface. Particulate farinaceous materials such as bran particles can also be employed to texturize the interior and/or surface of the biscuits and to provide other useful properties to the product. A dough found to produce biscuits highly palatable to dogs includes suitable proportions of wheat flour, wheat meal, soybean meal, meat and bone meal, animal fat and natural flavors in admixture with water. The meal used in the doughs suitable for production of biscuits useful in the invention can comprise meat and/or bone and/or vegetable matter including farinaceous materials, materials prepared from legumes such as bean and peas, tuberous materials such as potato meal, and the like. The means can be finely or coarsely ground as desired for the texture. Flours made from any suitable farinaceous material can be used.

The doughs generally have a water activity of about 0.90 and above upon completion of mixing of the dough ingredients. A suitable dough contains farinaceous material, an edible oil, an antioxidant, an antimycotic, salt, animal fat, added vitamins and minerals, such as those disclosed in U.S. Pat. No. 4,229,485, column 5, lines 7 to 57, which is incorporated herein by reference. The compositions of the invention also preferably contain at least one animal-derived proteinaceous meal such as meat meal, bone meal and fish meal. A good biscuit dough for producing the biscuits of the invention contains about 50 to 60 percent by weight wheat flour, about 5 to 10 percent by weight soybean meal, about 3 to 10 percent by weight meat meal and bone meal, about 1 to 5 percent wheat meal, about 1 to 5 percent animal fat preserved with BHA, about 20 to 30 percent by weight water, and about 2 to 5 percent by weight of natural flavors, vitamin and mineral preblend, and acidulant.

The dog biscuit doughs can contain a softening agent. Any suitable softening agent can be used. The preferred humectant is propylene glycol. Examples of other suitable humectants are corn syrup, sugar and polyalcohols, such as, sorbitol and glycerin. Any suitable humectant known in the art can be used.

The dough ingredients are generally mixed at a temperature of about 45° to about 140° F. preferably about 60° to about 125° F.

The dog biscuit dough for the outer portion and the inner portion can be mixed using any suitable or conventional equipment. For example, the mixing can be at 20 to 100 rpm. For example a dry blending step can be done typically at room temperature for a period of time of about 3 minutes to about 20 minutes. The dry-blended mixture can then be mixed with the hot water to form a first stage dough. The water which can be admixed with the dry-blended mixture is typically at a temperature of about 65° to about 150° F. The hot water can be added, with mixing, over a period of time of about 3 minutes to about 6 minutes to form the first stage dough. Then, the fat portion of the biscuit dough can be admixed with the first stage dough to form the final stage dough. The fat portion can be added at a temperature at which it is at least fluid, typically at about 100° to about 150° F. The fat portion can be mixed for a period of time which is sufficient to form a dough whose homogeneity is visually apparent. A typically final mixing time is about 3 to about 5 minutes.

Preparation of the dough is achieved at about atmospheric pressure with mixing of the components being conveniently achieved in an upright sigma blade mixer or other bakery-type mixers. The various ingredients can be added over a period of time or in a one-shot manner according to the above order of addition. However, melted fat and water can be added simultaneously and mixed for 6 to 10 minutes.

The dough can be formed into dough pieces using any suitable or conventional manner, such as, by extrusion, molding, stamping or cutting. Any suitable dog biscuit shapes can be used, such as, bone-shaped canine biscuits. Holes can be formed in the dog biscuits to facilitate the escape of moisture during baking, cooking and/or drying.

The dog biscuit dough pieces can be baked using any suitable or conventional equipment and conditions. For example, the dog biscuit dough pieces can be passed into an oven such as a conventional band oven where the biscuits are baked. The conveyor belts of the oven can be coated with an edible lubricant such as a natural or synthetic cooking oil or shortening to facilitate separation from the conveyor belts of the baked products. Temperatures in the range of about 300° to about 600° F. can be used.

The invention coating can be applied to the dog biscuit dough pieces before baking followed by baking at a low baking temperature of, say, about 300° to about 310° F. It prefers to apply the invention coating after the dog biscuit dough pieces have been baked.

The baked dog biscuits can also be subjected to subsequent drying at temperatures of about 200° to 400° F. (e.g., for 25 to 12 minutes), either within the baking oven or separately, to produce the desired moisture content. If dealing with coating dog biscuits which have been baked with the coating on the dog biscuits, the baked, coated dog biscuits should not be dried at a temperature at above about 300° F. Drying is usually done at a temperature of about 75° to 300° F. to achieve the desired moisture content (about 5 to 13 weight percent).

The invention coating is preferably applied to baked dog biscuits. The coating is preferably applied to the baked dog biscuits in the form of a liquefied coating formulation by any suitable means, such as dipping, spraying, etc. The coating can encompass all or part of the baked dog biscuits.

The coating formulation usually is viscous enough so that the coating formulation generally only coats the surface regions of the baked dog biscuits. The presence of coating in the surface regions of the baked dog biscuits helps to anchor the resultant coating and to prevent the coating from easily being separated from the baked dog biscuits during handling and shipping.

The coating slurry can be applied to the baked dog biscuits by any suitable means, such as, spraying, dipping, etc. The coating slurry is applied generally at a temperature of 45° to 200° F., preferably at about 60° to about 190° F., and most preferably at about 180° F., (the baked dog biscuits best having been cooled, or allowed to cool, to less than 200° F.). The coating slurry has a low microbial profile at such higher temperatures.

After treating the baked dog biscuits with the invention coating slurry, the coated baked dog biscuits are dried. While the coated, baked dog biscuits are preferably air dried, it is also advantageous to dry the coated animal food using applied heat, e.g., in a hot air oven at a temperature of say 75° to 300° F. (typically 250° F. for 20 minutes). The coated dog biscuits are dried to obtain coated dog biscuits having a water activity of 0.70 or less. On a weight basis, the moisture content of the final coated biscuit product is less than or equal to about 15 percent by weight and preferably about 10 to 12 percent by weight of the final biscuit at 70 percent relative humidity. The coated dog biscuits are shelf stable.

The animal food within the scope of this invention needs to have a sufficient integrity to not fall apart during processing and handling, especially, so that the coating can be applied, dried/baked, etc., without losing its integrity or cracking. The animal food is best in the form of pieces or the like, such as, kibbles, biscuits, snacks, etc. The animal food pieces can be made by any suitable forming means, such as, extruding, molding, stamping, etc. The invention composition is used to reduce and control tartar accumulation on canine teeth.

The animal food can be the dog food disclosed in commonly-owned, copending U.S. Ser. No. 242,292, filed on Sept. 9, 1988, entitled "Chewy Dog Snacks", the pertinent parts of which are incorporated herein by reference. A chewy, semi-plastic, non-extruded, non-porous, microbiologically-stable dog food which includes: 12 to about 30 weight percent, based upon the total weight of the dog food, of gelatin; at least one acidulant; at least one cereal starch-containing textural agent; at least one release agent; at least one taste agent; at least one sugar; salt; and added water. The dog food is in a molded form. The dog food has a pH of about 3 to 5, and has a moisture content of about 10 to 25 weight percent, based on the weight of the dog food. The process for preparing the dog food includes (a) mixing the dry components and liquid components with low speed agitation and continuing the mixing until a dough is obtained; (b) forming the dough by molding or rotary molding into molded snack or biscuit; (c) conditioning the molded dough at 185° to 200° F. for about 7 to 8 minutes; and (d) packaging the molded dog snack or biscuit in a protective package.

What is claimed is:

1. Process for the prevention of tartar accumulation on the teeth of a dog, comprising chewing or eating by the dog of a tartar inhibiting amount of raw hide which contains an edible coating comprising an effective anti-tartar amount of at least one alkali metal inorganic pyrophosphate, the amount of said at least one alkali metal inorganic pyrophosphate being sufficient to deliver from about 0.2 to about 5 weight percent, based on the total weight of the raw hide containing at least one alkali metal inorganic pyrophosphate, of $P_2O_7$, said at least one alkali metal inorganic pyrophosphate being water soluble, the raw hide containing an edible coating containing at least one alkali metal inorganic pyrophosphate being slightly acid to near neutral, and the raw hide containing an edible coating containing at least one alkali metal inorganic pyrophosphate being chewable, tough and flexible.

2. The process as claimed in claim 1 wherein the amount of said at least one alkali metal inorganic pyrophosphate is sufficient to deliver from 0.1 to 0.5 weight percent, based on the total weight of the raw hide containing at least one alkali metal inorganic pyrophosphate, of $P_2O_7$.

3. The process as claimed in claim 1 wherein said at least one alkali metal inorganic phosphate is a combination of trisodium monoacid pyrophosphate and tetrapotassium pyrophosphate, and the weight ratio of trisodium monoacid pyrophosphate to tetrapotassium pyrophosphate is between 0.01 to 99.99 and 99.99 to 0.01.

4. The process as claimed in claim 1 wherein the coating contains at least one surfactant or emulsifier which is lecithin or a modified lecithin surfactant, at least one suspension agent which is xanthan gum, a binding or adhesive agent which is a malto-dextrin, and a carrier which is a food starch or a modified food starch.

5. The process as claimed in claim 1 wherein the raw hide is in strip form.

* * * * *